United States Patent [19]

Sikes

[11] 4,160,825
[45] Jul. 10, 1979

[54] ANTIBODY-ACTIVE PROTEIN COMPOSITION

[76] Inventor: Dennis Sikes, 316 Beechwood Dr., Athens, Ga. 30601

[21] Appl. No.: 839,713

[22] Filed: Oct. 5, 1977

Related U.S. Application Data

[63] Continuation of Ser. No. 609,101, Aug. 29, 1975, abandoned, which is a continuation of Ser. No. 412,224, Nov. 2, 1973, abandoned.

[51] Int. Cl.² ............................................. A61K 39/00
[52] U.S. Cl. ................................. 424/85; 424/95
[58] Field of Search ............................................. 424/85

[56] References Cited

U.S. PATENT DOCUMENTS

| | | | |
|---|---|---|---|
| 3,461,200 | 8/1969 | Mathies | 424/85 |
| 3,664,994 | 5/1972 | Perper | 424/85 |

OTHER PUBLICATIONS

Camiener et al.–Progress in Drug Research, vol. 16 (1972), pp. 127 & 128.
Iwasaki et al.–Surgery, vol. 124 (1967), pp. 1–24.
Perper et al.–PSEBM, vol. 125 (1967), pp. 575–580.

*Primary Examiner*—Sam Rosen

[57] ABSTRACT

The preparation of a novel therapeutic composition useful in the treatment of rheumatoid arthritis and other hypersensitivity diseases and a method for using said composition is described.

9 Claims, No Drawings

ANTIBODY-ACTIVE PROTEIN COMPOSITION

This application is a continuation of Ser. No. 609,101, filed Aug. 29, 1975, which in turn was a continuation of Ser. No. 412,224, filed Nov. 2, 1973, both now abandoned.

The present invention is concerned with auto-immune diseases in warm blooded animals and is more particularly concerned with the auto-immune disease commonly referred to as rheumatoid arthritis and other hypersensitivity diseases, the preparation of a therapeutic composition useful in the treatment of warm blooded animals thus afflicted and a method for the use of the same.

The present invention is based on the discovery that warm blooded animals such as swine, dogs, deer, monkeys, cattle and horses afflicted with rheumatoid arthritis and other hypersensitivity diseases can be effectively treated with a novel therapeutic composition which is isolated from the serum of pregnant mares which have been hyperimmunized with a spleen cell preparation processed from spleens of healthy warm blooded animals.

It is known in the art that a host animal such as a rabbit, sheep, cow or horse can be hyperimmunized by the injection of an antigen from a warm blooded animal. Antigens which have been used include thymocytes, thoracic duct lymphocytes, lymph node cells, mesenteric lymph node cells and spleen cells, said antigens being obtained from mice, rats, guinea pigs, rabbits, dogs, monkeys, pigs and humans. After a period of time to allow antibody formation, the host animal is bled, the serum (ALS) separated from the whole blood and the serum fractioned by a selected physico-chemical means to separate the partially or completely purified anti-lymphocyte globulin (ALG). ALG contains the antibody-active immunoglobulins, the main fraction designated immunoglobulin G(IgG). The use of ALG produced as described hereinabove in humans has as its most obvious effect a direct cytotoxic action upon lymphocytes with resultant lymphopenia. This decrease in the proportion of lymphocytes in the blood can be accompanied by such undesirable side effects as cancer, serious viral infections and fungus infections.

The novel therapeutic composition of the present invention referred to hereinabove is an antibody-active composition whose molecular weight is in the area normally associated with ALG but which differs markedly from ALG heretofore prepared in that when said novel therapeutic composition is administered to warm blooded animals the undesirable cytotoxic action against lymphocytes usually associated with ALG is not characteristic of the material and there is no marked decrease in the proportion of lymphocytes in the blood of treated animals.

In the methods generally employed for the preparation of ALG the antigen which is used generally consists of selected viable lymphocytes. The antigen used in preparing the antibody-active composition of the present invention is a spleen cell preparation from spleens of healthy animals. There is no selectivity as regards the type of spleen cells used, all cells except erythrocytes present in the spleen being employed as the antigen. Furthermore, in procedures generally used for preparing ALG the antigens are normally administered for a short period of time and the ALG isolated from the host animal does not necessarily have a high titer. The antigen in the present invention is administered to healthy pregnant mares over a relatively long time period allowing the development of the novel therapeutic composition having a high antibody titer.

It is, therefore, a primary object of the present invention to provide a novel therapeutic composition which is an antibody-active composition. A further object is to provide a novel therapeutic composition which is an antibody-active composition and which is not cytotoxic to lymphocytes. Still further objects are to provide a novel therapeutic composition for the treatment of warm blooded animals suffering from rheumatoid arthritis or a hypersensitivity disease as, for example, mange, psoriasis and lupus erythematosus, and to provide a method of treating a warm blooded animal suffering from rheumatoid arthritis and a hypersensitivity disease. An additional object is to provide a method whereby the novel therapeutic composition of the present invention can be readily prepared. Additional objects of the invention will be readily apparent to one skilled in the art, and still other objects will become apparent hereinafter.

A description for preparing the novel composition and use of the same in the present invention follows.

Spleens which have been removed from healthy animals using aseptic techniques are cut into small blocks. The individual blocks (packed in ice if processed immediately, otherwise frozen) are homogenized in physiological saline solution, the spleen cells separated from the erythrocytes by centrifugation and the number of spleen cells per ml. determined using a hemocytometer. The spleen cell suspension which is adjusted to contain a known number of cells per ml. is administered over a prescribed time period to pregnant mares. The initial doses are administered intravenously and the final doses subcutaneously. The number of spleen cells given intravenously are gradually increased whereas the subcutaneous doses contain the same number of cells. Subsequent to the administration of the spleen cell suspension, the mares are bled weekly (100 ml./45 kg. body weight) until the agglutination titer falls below a predetermined value. The novel composition is isolated from the blood serum by a suitable physico-chemical means. The mares are rebred after foaling and after a rest period they are treated subcutaneously with the spleen cell suspension for further hyperimmunization. The cycle of rebreeding, hyperimmunization and bleeding can be repeated until the mares are no longer able to be bred. A spleen cell suspension from a different species can be used in subsequent hyperimmunizations. The novel composition after isolation from the blood sera of the hyperimmunized pregnant mares is administered subcutaneously on a weekly basis to warm blooded arthritic animals or animals with other hypersensitivity diseases until the titer to the respective diagnostic test and/or clinical manifestation disappears. During the treatment period of arthritic animals there is a gradual reduction in the evidence of pain and morning stiffness with increased locomotion and general appetite.

The foregoing general description for preparing and administering the novel composition of the present invention is applicable using spleens obtained from various animal species and the novel composition obtained from the pregnant mare serum can be used in warm blooded animals of various species which are afflicted with arthritis and/or other hypersensitive states.

In a preferred embodiment of the present invention the novel composition is prepared as set forth hereinafter.

PREPARATION OF SPLEEN CELL SUSPENSION

Whole intact spleens removed from healthy warm blooded animals by aseptic techniques are cut into small blocks weighing from 20 to 30 grams each. A block is put into a tared Virtis 45 homogenizing flask (10–400 ml. size), physiological saline solution (1 ml./gm. spleen) is added and the material homogenized at medium speed for several short 1-2 minute periods. The homogenate is filtered through two layers of sterile cheese cloth and the filtrate is centrifuged (1000×g) for 30 minutes at 4° C. The resulting multiphase solution comprising an erythrocyte layer, a buffy coat layer, and an upper layer is separated by aspiration. The erythrocyte layer is discarded. The retained upper layer and buffy coat layer is suspended in an equal volume of physiological saline solution, the suspension is gently mixed and the centrifugation repeated. The procedure is repeated until microscopic examination indicates that all erythrocytes have been removed. The final suspension is approximately four times the original volume and the number of cells per milliliter of the suspension is determined using a hemocytometer. The number of cells obtained from each spleen block (20-30 grams) varies from $6 \times 10^3$ to $2 \times 10^9$ cells per milliliter.

The spleen cell suspension prepared as above is sealed in glass vials (10 ml.) and stored at $-62°$ C. until used.

Sterility Check of Spleen Cell Suspension

A sample of the preparation is tested for viable microorganisms. The reticuloendothelial (RE) character of the suspension is determined by microscopic examination of a Giemsa obtained smear in order to determine that the number and type of cells are representative of a healthy spleen.

HYPERIMMUNIZATION OF PREGNANT MARES

The following procedure is used for hyperimmunization of a healthy pregnant mare of 3-4 years of age for said mare's first and second pregnancy. The procedure described for the second pregnancy is used for each successive pregnancy.

| Weeks | 1st Pregnancy |
|---|---|
| 1-13 | Primary Pregnancy Period. |
| 14-26 | Weekly IV Injections (13 injections) Initial injection $2 \times 10^6$; gradually increased to a final injection of $2 \times 10^8$ cells. |
| 27-39 | Triweekly SC injections (5 injections) $24 \times 10^8$ cells per injection. |
| 40-42 | Rest Period. |
| 43-47 | Bleeding Period: 100 ml. blood/45 kg. body wt. or until titer falls below $1:3 \times 10^6$ in a spleen cell agglutination test. |
| 48 | Mare foals. |
| 51 | Mare rebred. |

| Weeks | 2nd Pregnancy |
|---|---|
| 1-25 | Rest Period. |
| 26-32 | Weekly SC injections; $2 \times 10^8$ cells/injection. |
| 33-36 | Rest Period. |
| 37-47 | Bleeding Period: 100 ml. blood/45 kg. body wt. or until titer falls below $1:3 \times 10^6$ in a spleen cell agglutination test. |
| 48 | Mare foals. |

ISOLATION OF NOVEL COMPOSITION FROM SERUM

The novel composition of the present invention can be isolated from the blood serum of the hyperimmunized pregnant mare using physico-chemical techniques well known to the art such as salting out, alcohol precipitation, chromatography and precipitation using acridine bases. The following method describes the use of Diethylaminoethylamine (DEAE) Sephadex A-50 (Pharmacia Fine Chemicals, Piscataway, N.J.). DEAE Sephadex A-50 is a weakly basic anion exchanger which separates proteins in the molecular range of 30,000 to 200,000. The method is essentially that described by Perper et al. A rapid method for purification of large quantities of anti-lymphocyte serum. Proc. Soc. Exp. Biol. 125, 575:580 (1967).

The collected blood from the hyperimmunized pregnant mare remains at ambient temperature until maximum clot retraction. The serum is mixed with hydrated diethylaminoethylamine Sephadex A-50 (100 ml. of serum with 40 gm. of the Sephadex A-50) and the mixture is gently stirred for one hour at 4° C. The cold mixture is filtered through a Buchner funnel and the filtrate containing the novel composition further purified by two additional exposures to fresh portions of the Sephadex A-50.

The material is sterilized by millipore filtration and transferred aseptically to sterile screw cap vac vials and stored at $-62°$ C. or the sterilized material is lyophilized. The lyophilized material is also stored at $-62°$ C.

STANDARDIZATION OF NOVEL COMPOSITION

The potency of the novel composition is determined by spleen cells agglutination test and is standardized to contain a minimum titer of $1:3 \times 10^6$ with a protein concentration of approximately 1%.

The purity is determined by electrophoresis with cellulose acetate and acrylamide gel. Immunoelectrophoresis is done using equine anti-whole serum and anti-globulin fraction.

An analysis of the amino acid content of the novel composition for three species is set forth hereinbelow in table form.

| AMINO ACID MOLES/MOLE OF COMPOSITION | | | |
|---|---|---|---|
| Amino Acid | Equine anti-human | Equine anti-dog | Equine anti-pig |
| Tryptophan | 12 | 17 | 19 |
| Lysine | 68 | 80 | 78 |
| Histidine | 20 | 26 | 25 |
| Arginine | 28 | 33 | 37 |
| Aspartic Acid | 83 | 89 | 89 |
| Threonine | 105 | 99 | 105 |
| Serine | 137 | 99 | 147 |
| Glutamic Acid | 90 | 114 | 112 |
| Proline | 94 | 79 | 91 |
| Glycine | 92 | 94 | 93 |
| Alanine | 85 | 72 | 67 |
| Half Cystine | 22 | 26 | 10 |
| Valine | 117 | 123 | 103 |
| Methionine | 8 | 11 | 9 |
| Isoleucine | 26 | 36 | 35 |
| Leucine | 95 | 93 | 81 |
| Tyrosine | 52 | 48 | 46 |
| Phenylalanine | 50 | 44 | 34 |
| | 1184 | 1183 | 1181 |

The novel composition which is standardized to have a titer of $1:3 \times 10^6$ (spleen cell agglutination test) with a protein concentration of 1% or less is diluted to a volume of 10 ml. with physiological saline prior to administration to diseased animals. The method of administration can be subcutaneous or intravenously.

The dose per diseased animal varies with the diseased state and the size of the animal. The dose can vary from 5 ml. to 200 ml. The selected dose is administered weekly for a period of from five weeks to ten weeks. The onset of clinical improvement varies depending on the initial diseased state but improvement is generally seen within the first few weeks.

Control animals for comparative testing were either those which had been experimentally infected with *Erysipelothrix insidiosa* (*E. insidiosa*) or had developed polyarthritis under natural circumstances. In marked contrast to the animals which were treated with the novel composition and showed steady improvement during the treatment period, the control animals became progressively worse, were unable to stand and obtain feed and water without assistance. Blood samples were obtained weekly from both treated and control animals.

The lymphocyte count of the animals treated with the novel composition remained within normal limits. The blood of the diseased animals having polyarthritis was initially positive to the RA Test and RA Slide Test (RA = rheumatoid arthritis) but became negative to said tests after two to four weeks of treatment.

The examples set forth hereinafter are representative and relate both to control and diseased animals. The diseased animals were treated with the novel therapeutic composition of the instant invention. The novel therapeutic composition was administered to approximately 40 animals, including swine, monkeys, dogs, deer, cattle and horses. The examples are representative of the results obtained for all the diseased animals. Blood analyses were run on all animals weekly. The lymphocyte counts given in the examples show that the therapeutic composition of the present invention when administered to diseased animals does not cause cytotoxicity as measured by leukopenia.

Identical blood analyses were run on all animals. The following table is representative and is the analyses carried out on the diseased 3 year old barrow of Example 4 during the treatment period.

"Old Man"—
Three year old barrow. Experimentally infected with *E. insidiosa* at four months of age. Developed advanced polyarthritis which persisted. Received 80 ml of whole pig spleen cell antiserum of equine origin with a titer of 1:3,000,000. Clinical arrest — improved appetite and great mobility. Necropsy — ankyiosis of carpal, tarsal, and 6th lumbar joints. Healed synovial membranes. Other tissue normal.

| Weeks | 1 | 2 | 3 | 4 | 5 |
|---|---|---|---|---|---|
| Treatment | 80 ml | 80 ml | 80 ml | 80 ml | 80 ml |
| Hematocrit | 43.0 | 40.0 | 38.0 | 40.0 | 39.0 |
| Hemoglobin | 14.0 | 13.6 | 12.9 | 12.3 | 12.5 |
| White Blood Count | 16,000 | 16,900 | 16,500 | 18,000 | 17,100 |
| Segments | 30.5 | 46.0 | 52.5 | 35.5 | 32.5 |
| Non Seg (Band) | 1.0 | 7.0 | 2.5 | 3.5 | 2.5 |
| Lymphocytes | 56.0 | 44.0 | — | 53.0 | 56.5 |
| Monocytes | 3.0 | 0.5 | 1.0 | 3.0 | 1.5 |
| Eosinophils | 9.5 | 2.5 | 7.0 | 5.0 | 7.0 |
| Basophils | — | — | 2.0 | — | — |
| E.S.R. | 20 mm/hr | 13.5 mm/hr | 37 mm/hr | 14 mm/hr | 15 mm/hr |
| Prothrombin | 11.4 | 12.3 | 13.0 | 14.1 | 13.9 |
| MCH | 20.0 | 20.5 | 19.5 | 19.5 | 19.5 |
| MCV | 60.0 | 61.0 | 59.0 | 65.0 | 61.5 |
| MCHC | 34.0 | 34.0 | 34.0 | 31.0 | 32.0 |
| E. Tube Test | 1:640 | 1:640 | 1:640 | 1:640 | 1:640 |
| Swine RA Test | 1:10,000 | 1:10,000 | Neg. | Neg. | Neg. |
| RA Slide Test | 1:20 | 1:20 | 1:20 | Neg. | Neg. |
| Total Protein | 8.8 gm | 9.3 gm | 8.7 gm | 8.9 gm | 8.8 gm |
| Albumin | 2.7 gm | 2.5 gm | 2.3 gm | 2.4 gm | 2.3 gm |
| Globulin | 6.1 gm | 6.8 gm | 6.4 gm | 6.5 gm | 6.5 gm |
| Gamma Globulin | 28.7% | 32.0% | 31.9% | 31.9% | 29.7% |
| Beta Globulin | 18.9% | 24.4% | 21.3% | 23.5% | 19.0% |
| Alpha 2 | 22.9% | 18.4% | 20.9% | 20.0% | 21.4% |
| Alpha 1 | 2.2% | 3.2% | 3.4% | 2.3% | 1.5% |

| Weeks | 6 | 7 | 8 | 9 | 10 |
|---|---|---|---|---|---|
| Treatment | 80 ml | 80 ml | 80 ml | 80 ml | 80 ml |
| Hematocrit | 38.0 | 37.5 | 38.5 | 40.5 | 39.5 |
| Hemoglobin | 12.5 | 12.1 | 12.9 | 12.5 | 12.5 |
| White Blood Count | 23,100 | 17,600 | 12,900 | 13,200 | 15,700 |
| Segments | 40.5 | 36.0 | 26.0 | 10.0 | 35.0 |
| Non Seg (Band) | 2.5 | 1.0 | 0.5 | — | — |
| Lymphocytes | 49.5 | 53.0 | 68.0 | 81.0 | 56.5 |
| Monocytes | 1.5 | 1.5 | 1.0 | 1.0 | 1.0 |
| Eosinophils | 5.0 | 8.5 | 4.5 | 8.0 | 7.5 |
| Basophils | 2.0 | — | — | — | — |
| E.S.R. | 12 mm/hr | 27 mm/hr | 32 mm/hr | 32 mm/hr | 28 mm/hr |
| Prothrombin | 12.5 | 11.9 | 12.0 | 9.8 | 10.6 |
| MCH | 20.0 | 21.2 | 21.5 | 19.5 | 19.3 |
| MCV | 61.0 | 65.7 | 64.0 | 63.2 | 66.6 |
| MCHC | 33.0 | 32.0 | 33.5 | 31.2 | 32.0 |
| E. Tube Test | 1:160 | 1:80 | 1:80 | 1:160 | 1:80 |
| Swine RA Test | Neg. | Neg. | Neg. | Neg. | Neg. |
| RA Slide Test | Neg. | Neg. | Neg. | Neg. | Neg. |

-continued

"Old Man"—
Three year old barrow. Experimentally infected with *E. insidiosa* at four months of age. Developed advanced polyarthritis which persisted. Received 80 ml of whole pig spleen cell antiserum of equine origin with a titer of 1:3,000,000. Clinical arrest — improved appetite and great mobility. Necropsy — ankyiosis of carpal, tarsal, and 6th lumbar joints. Healed synovial membranes. Other tissue normal.

| Total Protein | 9.1 gm | 8.8 gm | 9.0 gm | 9.7 gm | 9.4 gm |
|---|---|---|---|---|---|
| Albumin | 2.1 gm | 2.3 gm | 2.4 gm | 2.5 gm | 2.5 gm |
| Globulin | 7.0 gm | 6.5 gm | 6.6 gm | 7.2 gm | 6.9 gm |
| Gamma Globulin | 33.7% | 31.7% | 36.4% | 36.2% | 37.4% |
| Beta Globulin | 23.2% | 26.6% | 18.3% | 23.0% | 20.7% |
| Alpha 2 | 20.5% | 17.8% | 18.3% | 17.0% | 19.2% |
| Alpha 1 | 2.6% | 2.4% | 2.0% | 1.8% | 2.1% |

EXAMPLE 1

A 3 year old barrow which had been experimentally infected with *E. insidiosa* at four months of age developed advanced polyarthritis which persisted. The barrow was unable to stand when helped up and feed and water had to be put in the side of its mouth. The lymphocyte count for a ten week period was 52.0, 51.0, 39.0, 45.5, 57.0, 48.5, 38.5, 43.0 and 52.5.

EXAMPLE 2

A 3 year old barrow which had been experimentally infected with *E. insidiosa* at four months of age developed advanced polyarthritis which persisted. The barrow was treated for a ten week period with normal horse serum fractionate (80 ml. per treatment). The barrow became progressively worse, developed psoriasis, became very lame and was unable to get up. The lymphocyte count was 41.0, 40.0, 37.0, 52.0, 41.0, 45.5, 38.0, 30.0, 52.0 and 50.5.

EXAMPLE 3

The barrow from the previous example (Example 2) which had served as a control animal and had received normal horse serum fractionate without improvement was treated with pig spleen cell antiserum fractionate of equine origin having a titer of 1:3,000,000 for a treatment period of eight weeks. The weekly dose for the first five weeks was 80 ml. and for the last three weeks was 40 ml. During the treatment period there was clinical arrest with improved appetite and greater mobility. The lymphocyte count was 30.0, 52.0, 50.5, 37.5, 34.0, 47.0, 50.0 and 57.0.

EXAMPLE 4

A 3 year old barrow which had been experimentally infected with *E. insidiosa* at four months of age developed advance polyarthritis which persisted. The barrow received 80 ml. weekly of pig spleen cell antiserum fractionate of equine origin having a titer of 1:3,000,000. There was clinical arrest of the polyarthritis with concomitant improved appetite and greater mobility. The barrow was sacrificed and necropsy showed ankylosis of carpal, tarsal, and 6th lumbar joints. The necropsy showed healed synovial membranes. Other tissue was normal. During the course of treatment the lymphocyte count was 56.0, 44.0, 35.0, 53.0, 56.5, 49.5, 53.0, 68.0, 81.0 and 56.5.

EXAMPLE 5

A 5 year old hound cross breed male which had been experimentally infected with *E. insidiosa* developed polyarthritis which persisted. The dog received 20 ml. of dog spleen cell antiserum fractionate of equine origin for a 10 week period having a titer of 1:3,000,000. There was clinical arrest of the polyarthritis with improved appetite and greatly improved mobility. The lymphocyte count was 45.5, 56.0, 32.5, 38.5, 35.0, 30.0, 33.0, 36.0, 20.0 and 28.0.

EXAMPLE 6

A Great Dane 10 months of age and weighing 105 lbs. developed naturally occurring polyarthritis and was unable to stand up. The dog was treated weekly for a period of ten weeks with 40 ml. weekly of pig spleen cell antiserum fractionate of equine origin having a titer of 1:3,000,000. There was clinical arrest of the polyarthritis with improved appetite and increased mobility. Necropsy showed healed synovial tissue with all other tissues normal. The lymphocyte count was 22.5, 15.5, 25.5, 25.0, 33.5, 29.5, 29.0, 24.5 and 24.5.

EXAMPLE 7

A 3 year old German Shepherd which was very lame in all legs as the result of naturally occurring polyarthritis received 40 ml. of pig spleen cell antiserum fractionate of equine origin weekly having a titer of 1:3,000,000. The animal had had prolonged steroid therapy prior to the treatment period with no improvement. During the ten week treatment period there was clinical arrest of the polyarthritis with improved appetite and greater mobility. The lymphocyte count was 34.5, 29.0, 18.0, 27.0, 31.5, 20.5, 22.0, 17.0, 28.0 and 25.5.

EXAMPLE 8

A 5 year old pointer had advanced polyarthritis of one year duration and walked on its front legs with its rear legs held up. The dog had a severe case of glomerulonephritis ten days before the treatment period and had prolonged steroid therapy prior to treatment. The pointer was given weekly injections of 40 ml. of pig spleen cell antiserum fractionate of equine origin having a titer of 1:3,000,000. The polyarthritis was arrested, the pointer had improved appetite and regained the ability to run on all four legs. Necropsy showed healed synovial membranes and glomerulonephritis cystitis. The lymphocyte count was 10.5, 22.5, 9.5, 16.0, 16.5, 22.0, 26.0, 15.0, 27.5 and 21.5.

EXAMPLE 9

An old male monkey which was unable to climb cage walls due to arthritis received 5 ml. of pig spleen cell antiserum fractionate of equine origin having a titer of 1:3,000,000 for ten weeks. There was clinical arrest of the arthritis with improved appetite and improved mobility. The monkey had ankylosis of the hips and the lumbar spine. The lymphocyte count was 21.5, 39.0, 22.5, 26.5, 30.5, 18.5, 20.5, 19.0, 16.0 and 18.0.

EXAMPLE 10

A monkey several yars old and unable to climb cage walls due to arthritis was given 5.0 ml. of pig spleen cell antiserum fractionate of equine origin having a titer of 1:3,000,000. At the end of the six week treatment period there was clinical arrest of the arthritis with improved appetite and great mobility. The lymphocyte count was 44.0, 46.0, 28.0, 50.0, 41.0 and 31.0.

EXAMPLE 11

A two year old short haired mongrel dog had demodetic mange on both sides of the face and the two front legs. The remaining hair on the left side of the face was removed. Mongeol, a preparation of Chlordane and benzoyl benzoate was applied topically daily. On the same day the topical application of Mangeol was started the dog was given subcutaneously 10 ml. of pig spleen cell antiserum fractionate of equine origin having a titer of 1:3,000,000. After the first injection improvement was noted and at the end of three weeks (post 3rd injection) there was marked improvement with the major portion of the lesions originally present no longer in evidence and the dog presenting a normal healthy appearance. The left side of the face which had been treated with Mangeol was free of mites. Mites were recovered from the right side of the face and the two front legs.

From the foregoing description and examples it can readily be seen by those skilled in the art that the present invention discloses a novel therapeutic composition, a novel method of treating warm blooded animals, and a method for producing said composition which is useful in the treatment of warm blooded animals afflicted with rheumatoid arthritis and hypersensitivity diseases.

What is claimed is:

1. A method for producing an antibody-active protein composition which comprises administering a spleen cell preparation from a heterologous warm blooded species to a pregnant mare to hyperimmunize the mare, removing blood from the hyperimmunized mare, separating the clear serum from the blood, and fractionating said serum by a physical-chemical procedure to separate therefrom said antibody-active protein fraction.

2. An antibody-active protein composition produced according to claim 1 having therapeutic properties for the treatment of rheumatoid arthritis and hypersensitivity diseases in warm blooded animals, said antibody-active protein composition being non-cytotoxic to lymphocytes.

3. A method of claim 1 wherein the physical-chemical procedure is chromatography, salting out or the employment of acridine bases.

4. A method in accordance with claim 1 wherein the spleen cell preparation is prepared from pig spleen.

5. A method in accordance with claim 1 wherein the spleen cell preparation is prepared from dog spleen.

6. A method in accordance with claim 1 wherein the spleen cell preparation is prepared from human spleen.

7. A method of treating a warm blooded animal suffering from rheumatoid arthritis or a hypersensitivity disease which comprises administering to said animal an antibody-active protein composition in accordance with claim 2 having a spleen cell agglutination titer of 1 to 3,000,000 and a protein concentration of approximately 1 percent.

8. A method in accordance with claim 7 wherein the antibody-active protein composition is administered subcutaneously.

9. A method in accordance with claim 7 wherein the antibody-active protein composition is administered intravenously.

* * * * *